United States Patent [19]

Beale

[11] 4,347,842

[45] Sep. 7, 1982

[54] DISPOSABLE ELECTRICAL SURGICAL SUCTION TUBE AND INSTRUMENT

[76] Inventor: Mark Beale, 111 Old Hickory Blvd. No. 170, Nashville, Tenn. 37221

[21] Appl. No.: 121,669

[22] Filed: Feb. 15, 1980

[51] Int. Cl.³ .............................................. A61M 1/00
[52] U.S. Cl. ................................. 128/276; 128/303.13
[58] Field of Search ......... 174/47; 339/182 R, 182 L, 339/182 T, 182 RS, 182, 91 R, 184 M; 128/276, 275.1, 303.17, 303.16, 303.15, 303.14, 303.13, 419 R, 275

[56] References Cited

U.S. PATENT DOCUMENTS

| | | | |
|---|---|---|---|
| 3,295,514 | 1/1967 | Hein et al. | 128/303.17 |
| 3,641,479 | 2/1972 | O'Brien | 339/182 R |
| 3,662,151 | 5/1972 | Haffey | 128/303.14 |
| 3,768,487 | 10/1973 | Rose | 128/419 P |
| 3,828,780 | 8/1974 | Morrison, Jr. | 128/303.17 |
| 3,902,494 | 9/1975 | Haberlen et al. | 128/303.17 |
| 3,906,955 | 9/1975 | Roberts | 128/275.1 |
| 3,974,833 | 8/1976 | Durden | 128/303.17 |
| 4,165,147 | 8/1979 | Buck | 339/182 R |

Primary Examiner—Robert W. Michell
Assistant Examiner—J. L. Kruter
Attorney, Agent, or Firm—Harpman & Harpman

[57] ABSTRACT

An expendable electrosurgical flexible suction tube for use with a cauterizer surgical instrument which combines the suction and power supply utilized in micro electrosurgical procedures. The disposable suction tube has metallic electrical contacts built in that provide resilient connections with spaced annular metal contacts in an instrument. Power supply wires for the contacts in the tubes are embedded in the non-conductive material of the tube.

4 Claims, 5 Drawing Figures

4,347,842

DISPOSABLE ELECTRICAL SURGICAL SUCTION TUBE AND INSTRUMENT

BACKGROUND OF THE INVENTION (1) Field of the Invention

The present invention relates to microsurgical flexible suction tubes used to draw tissue matter and liquids during electrosurgical procedures.

(2) Description of the Prior Art

Prior devices have used a variety of different electrosurgical tools and suction combinations. See for example U.S. Pat. Nos. 3,974,833; 3,902,494 and 3,828,780.

In U.S. Pat. No. 3,974,833, a disposable electrical surgical cautery with suction control feature is shown wherein suction and power are supplied separately to a single non-interchangeable tool.

Applicant's device combines power and suction means in a resilient multiple tool receptacle end of a suction tube.

In U.S. Pat. No. 3,902,494, a suction surgical instrument is shown having an electrode near the suction tube to prevent clogging of the suction port.

Applicant's invention encloses in the resilient end portion of a suction tube, a pair of flexible electrical contacts to provide power to a variety of microsurgical tools that can be attached to the tube combining positive power and suction connections.

U.S. Pat. No. 3,828,780 discloses an electrocoagulator-suction instrument having an open ended metal tube that is inserted in an instrument for contact with the suction passageway and an exposed wire is provided. Separate suction and electrical lines supply suction and power to the instrument.

Applicant's device provides a suction and power source in a single device for use with instruments that are interchangeably positioned in the end of the suction tube.

SUMMARY OF THE INVENTION

An expandable, electrosurgical suction tube and instrument holder for use in microsurgery has a receptacle in one end that provides both power and suction to a variety of surgical instruments that can be connected thereto. A pair of resilient metallic contacts are enclosed within the non-conductive receptacle end of the suction tube for positive contact with a pair of annular metallic contacts on the instrument used. Suction capability is maintained in the instrument by apertured annular contacts on the instrument which distort the resilient contacts when engaged thereagainst and provide a passageway for the suction.

DESCRIPTION OF THE PREFERRED EMBODIMENT

Figure 1:
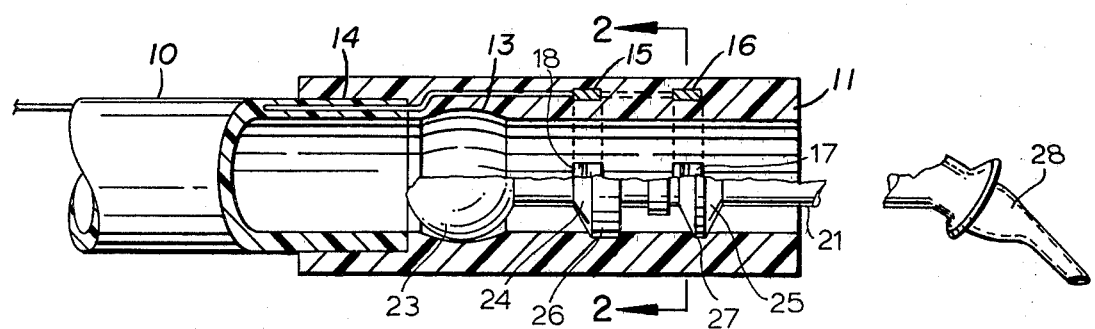
FIG. 1 is a side elevation with parts in cross section showing the instrument receiving end of the suction tube.

The instrument receiving end of a disposable electrosurgical suction and electrical power supply tube for surgical instruments is seen in FIG. 1 of the drawings as comprising an elongated flexible tube 10 having a resilient tubular body member 11 on one end thereof. The body member 11 has an open end 12, a spaced annular groove 13 is formed in the body member 11 inwardly of the end 12. The tube 10 is of an outside diameter capable of being received and secured within an area of increased diameter 14 in the tubular member 11. The tube 10 and the tubular body member 11 are formed of an electrically non-conductive material such as a synthetic resin. A pair of electrical terminals 15 and 16 are partially embedded in the tubular body member 11.

Figure 2:
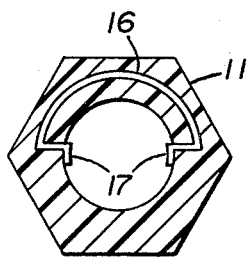
FIG. 2 is a cross section on line 2—2 of FIG. 1.
Figure 4:
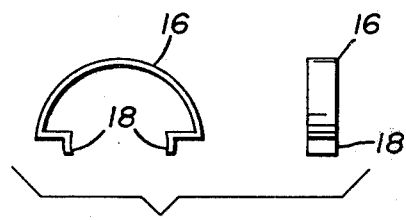
FIG. 4 is a combined front and side view of one of the contacts seen in FIGS. 1 and 2.
Figure 5:
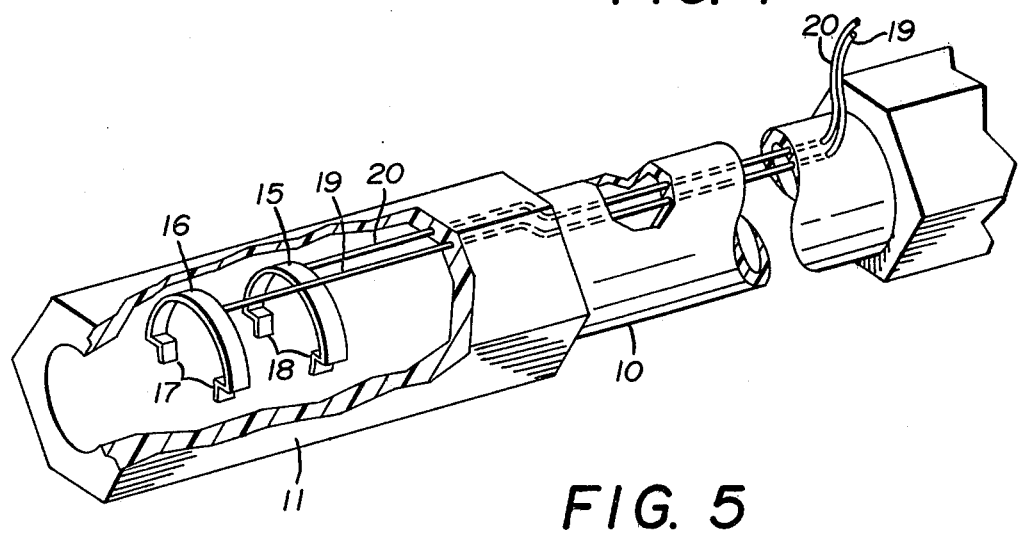
FIG. 5 is a cutaway perspective view of the end portion of the suction and power supply tube of the invention.

Referring now to FIGS. 2, 4 and 5 of the drawings, each of said electrical terminals 15 and 16 comprises an arcuate band of conductive material having ends 17 and 18 that are inwardly and downwardly shaped providing a pair of oppositely exposed contact portions 19 and 20 which extend along the hollow interior of said body member 11.

Figure 3:
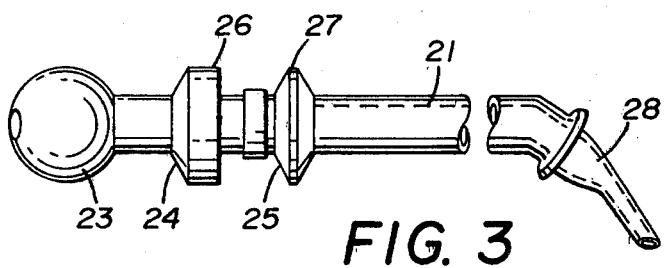
FIG. 3 is a side view of an instrument for use with the suction tube of FIG. 1.

As seen in FIGS. 1 and 5 of the drawings, each of said terminals 15 and 16 has electrical conductors 19 and 20 extending through said body members 10 and 11. Said conductors 19 and 20 supply power to an instrument which is shown in FIG. 3 of the drawings. The instrument is comprised of a tubular shaft 21 having an apertured spherical end 23 of a diameter to allow for insertion into the open end 12 of the tubular member 11 to provide an air tight fit therein.

A pair of annular contacts 24 and 25 are positioned on the instrument shaft 21 in spaced relation to each other inwardly from the spherical end 23. The annular contacts 24 and 25 have flat annular surfaces 26 and 27 respectively which engage said contacts 17 and 18 when said instrument is inserted within the tubular body member 11. The spherical end 23 registers with the annular groove 13 in the tubular body member 11 to insure registry of the annular surfaces 26 and 27 with the contacts 17 and 18 respectively. in this example, the instrument shaft 21 has a cautery end 28 affixed thereto. The insertion of the instrument shaft 21 within the end 12 of the tubular body member 11 completes an air tight interior passageway from the suction tube device and through said apertured spherical end 23 which is in communication with the instrument body defined by said tubular shaft 21. The conductors 19 and 20 are engaged at points midway between the ends 17 and 18 of the arcuate bands 15 and 17 allow the same to flex relative to one another when the instrument shaft 21 is positioned within the body member 11.

The instrument used can be anyone of a variety of different micro electrosurgical instruments having configurations which will give the surgeon both suction to remove tissue and liquid matter and an electric cutting or cauterization tool without the need of separate power and suction lines which become of ever increasing importance to the micro surgical field where space is at a premium.

The suction line defined by the tube 10 is connected to a vacuum machine, not shown, in the usual manner, while the conductors 19 and 20 within the secondary tubular body member 14 emerge as at 29 therefrom and are connected to an electrical surgical power generator (not shown) as will be apparent to one skilled in the art.

Thus it will be seen that a new and useful device has been illustrated and described, and various modifications may be made therein without departing from the spirit of the invention.

What I claim is:

1. The combination of an expandable electrosurgical suction tube comprising an elongated flexible tubular body member, a receptacle and on said tube, an annular groove within said receptacle end, electric contact means within said receptacle end, conductors for electrical current within said tubular body member, an annular groove in said receptacle end, said receptacle end being resilient; and an electrosurgical instrument comprising a hollow shaft, a hollow cautery on one end of said hollow shaft, an apertured sphere on the other end of said hollow shaft and a pair of spaced annular contacts on said hollow shaft inwardly from said apertured sphere, said apertured sphere on said hollow shaft adapted to register in said annular groove in said receptacle end to align said annular contacts with said electric contact means within said receptacle end.

2. An expendable electrosurgical suction tube comprising an elongated flexible tube, a resilient receptacle end on said tube, an annular groove within said receptacle end, spaced electrical terminals within said receptacle end, conductors for electrical current within said tube and said receptacle end for an electrosurgical instrument having spaced electrical contacts and an apertured spherical fitting on one end for snap-in registration in said annular groove, said receptacle end and said tube made of nonconductive material such as synthetic resin, said electrical terminals consisting of arcuate bands embedded in said receptacle end and having exposed inwardly and downwardly shaped ends and formed of a flexible electrical conductive material.

3. The expendable electrosurgical suction tube of claim 1 wherein said electrical contacts on said electrosurgical instrument are annular and have flat annular surfaces.

4. The expendable electrosurgical suction tube of claim 1 wherein said electrical contacts on said surgical instrument are annular and in spaced relation to one another and having flat annular surfaces and are spaced with respect to said apertured spherical fitting.

* * * * *